United States Patent [19]
Cocciantelli et al.

[11] Patent Number: 5,902,699
[45] Date of Patent: May 11, 1999

[54] METHOD OF CHARACTERIZING AN ELECTRODE BINDER

[75] Inventors: Jean-Michel Cocciantelli, Bordeaux; Isabelle Coco; Jean-Jacques Villenave, both of Talence, all of France

[73] Assignee: Saft, Romainville, France

[21] Appl. No.: 08/900,284

[22] Filed: Jul. 25, 1997

[30] Foreign Application Priority Data

Jul. 26, 1996 [FR] France .................................. 96 09451

[51] Int. Cl.$^6$ ..................................................... H01M 4/62
[52] U.S. Cl. ......................... 429/217; 429/212; 429/218; 204/294; 204/280; 29/623.5
[58] Field of Search .................................. 429/212, 217, 429/218; 29/623.5; 204/294, 280

[56] References Cited

U.S. PATENT DOCUMENTS

| | | | |
|---|---|---|---|
| 3,507,773 | 4/1970 | Grangaard | 204/294 |
| 5,527,638 | 6/1996 | Kinoshita et al. | 429/217 |
| 5,631,100 | 5/1997 | Yoshino et al. | 429/217 |
| 5,691,085 | 11/1997 | Coco et al. | 429/217 |

FOREIGN PATENT DOCUMENTS

| | | |
|---|---|---|
| 0435635A2 | 7/1991 | European Pat. Off. . |
| 0740355A1 | 10/1996 | European Pat. Off. . |
| 1415089 | 11/1975 | United Kingdom . |
| WO9307464 | 4/1993 | WIPO . |

OTHER PUBLICATIONS

F. M. Fowkes et al, Attractive Forces at Interfaces, *Industrial and Engineering Chemistry,* vol. 56, 1964, pp. 40–52.

*Primary Examiner*—Bruce F. Bell
*Attorney, Agent, or Firm*—Sughrue, Mion, Zinn, Macpeak & Seas, PLLC

[57] ABSTRACT

In a method of characterizing a polymer binder for cell electrodes in contact with an electrolyte and including a current collector and a paste containing an electrochemically active material and said binder, a spreading coefficient of the binder on the active material is calculated from the measured angle of contact between standard liquids and the active material and the binder, respectively. An interaction energy of the binder with the electrolyte is calculated from the measured angle of contact between the electrolyte and the binder. The binder is selected such that the spreading coefficient is less than zero and the interaction energy is at least 60 mJ/m$^2$.

3 Claims, 1 Drawing Sheet

METHOD OF CHARACTERIZING AN ELECTRODE BINDER

BACKGROUND OF THE INVENTION

1. Field of the Invention

The present invention concerns a method of characterizing an electrode binder. It further encompasses the binder selected by this method and the electrodes containing it.

2. Description of the Prior Art

A plasticized (non-sintered) electrode comprises a support serving as a current collector coated with a paste containing the powdered active material and a binder, to which a conductive material may be added.

The function of the binder is to assure the cohesion of the grains of active material to each other and to the support of the electrode prior to assembly of the storage battery and during its operation. The binder must have sufficient chemical stability vis á vis the components of the cell; the adhesive properties of some binders deteriorate upon cycling. The binder must also be capable of accommodating dimensional variations of the electrode during cycling throughout its service life.

Another function of the binder is to maintain the electrical contact between the grains of active material and to favor ion exchange with the electrolyte. The electrochemically active surface area of an electrode depends on the surface area wetted by the electrolyte. If the electrode is insufficiently wetted the active surface area is reduced, which leads to an increase in the local current density and a lower charged capacity. To promote wetting of the electrode by the aqueous electrolyte the binder must have a hydrophilic character. The surface area accessible to the electrolyte depends on how the grains of active material are coated and bound by the polymer. The polymer film must have discontinuities enabling electron exchange.

At present, choosing an appropriate binder is based on an electrochemical evaluation under real conditions of use. The low concentration of binder used in the fabrication of an electrode necessitates long-term tests to show up the differences in performance between electrodes including the various binders to be evaluated. Under these conditions, optimizing the composition of the electrodes is a slow and random process, which considerably limits the possibilities of improving the batteries.

An aim of the present invention is to propose a method of selecting a binder to be used in the composition of an electrode and conferring high performance on it throughout its period of use.

Another aim of the invention is to propose a fast and easy method of choosing an electrode binder.

SUMMARY OF THE INVENTION

The present invention consists of a method of characterizing a polymer binder for cell electrodes in contact with an electrolyte including a current collector and a paste containing an electrochemically active material and said binder, comprising the following steps:

- a spreading coefficient of said binder on said active material is calculated from a measured angle of contact between standard liquids and said active material and said binder, respectively,
- an interaction energy $I_{EL}$ of said binder with said electrolyte is calculated from a measured angle of contact between said electrolyte and said binder, and
- said binder is selected such that said spreading coefficient is less than zero and said interaction energy is at least 60 mJ/m$^2$.

The spreading coefficient $\lambda$ of the binder defined as follows:

$$\lambda = \gamma_{AM} - \gamma_{binder} - \gamma_{AM/binder}$$

in which $\gamma_{AM}$ and $\gamma_{binder}$ are the surface energies of the active material and the binder, respectively, and $\gamma_{AM/binder}$ is the interface energy between the active material and the binder.

The surface energy is measured by the sessile drop method (G. KRUSS: "Manuel d'utilisation du goniométre"), that is to say by measuring the angle of contact of a drop of a reference liquid, the surface tension of which is known, deposited on the surface of the active material or of a film of binder. The quality of the measurement of the contact angle $\Theta_{AM}$ or $\Theta_{binder}$ is principally dependent on the following parameters: a solid, clean and smooth surface, and reference liquids of the highest possible purity.

The surface energy $\gamma_{AM}$ of the active material satisfies the following equation:

$$\gamma_{AM} = \gamma^{Lw}{}_{,AM} + 2\sqrt{\gamma^+{}_{,AM} \cdot \gamma^-{}_{,AM}}$$

where $\gamma^{Lw}{}_{,AM}$ is the dispersive component corresponding to Van der Waals interactions and $\gamma^{DA}{}_{,AM} = 2\sqrt{\gamma^+{}_{,AM} \cdot \gamma^-{}_{,AM}}$ is the component corresponding to the acid-base interaction (electron donor/acceptor).

The dispersive component $\gamma^{Lw}{}_{,AM}$ is measured using the method described by F. M. FOWKES (Ind. Eng. Chem., 56, 1964, 12–14). The reference liquid used is an apolar liquid such as α-bromonaphthalene, diiodomethane, tricresyl phosphate, dioxolane or an alkane. In this case, $\gamma^{DA}{}_{,AM} = 0$ and $\gamma_{AM} = \gamma^{Lw}{}_{,AM}$ where $\gamma^{Lw}{}_{,AM}$ is a function of the angle of contact $\Theta_{AM}$ of the apolar liquid with the active material.

The non-dispersive component is measured using reference liquids which are polar liquids for example water or ethyleneglycol, the acidic and basic characteristics of which are known (R. S. GOUD and C. S. VAN OSS in "Modern approaches to wettability—Theory and applications", M. E. SCHRADER AND G. I. LOEB, Ed. Plenum Press, N.Y., 1992). For each liquid, an acidic component $\gamma^+{}_{,AM}$ and a basic component $\gamma^-{}_{,AM}$ are calculated from the measured angle of contact of the polar liquid with the active material.

The surface energy $\gamma_{binder}$ of the binder satisfies the following equation:

$$\gamma_{binder} = \gamma^{Lw}{}_{,binder} + 2\sqrt{\gamma^+{}_{,binder} \cdot \gamma^-{}_{,binder}}$$

where $\gamma^{Lw}{}_{,binder}$ is the dispersive component and $\gamma^{DA}{}_{,binder} = 2\sqrt{\gamma^+{}_{,binder} \cdot \gamma^-{}_{,binder}}$ is the component corresponding to the acid-base interaction. These two components are determined for the binder in the same way as described previously for the active material.

Finally, the interface energy $\gamma_{AM/binder}$ is calculated from the surface energies $\gamma_{AM}$ and $\gamma_{binder}$ using the equation:

$$\gamma_{AM\backslash binder} = \gamma_{AM} + \gamma_{binder} - 2\sqrt{\gamma^{Lw}{}_{,AM} \cdot \gamma^{Lw}{}_{,binder}}{}_{AM} - 2\sqrt{\gamma^+{}_{,AM} \cdot \gamma^-{}_{,binder}} - 2\sqrt{\gamma^-{}_{,AM} \cdot \gamma^+{}_{,binder}}$$

The interaction energy $I_{EL}$ is defined as follows (N. K. ADAME: "Physics on a chemistry of surfaces", 3rd Ed., Oxford University Press, London, 1941):

$$I_{EL} = \gamma_{EL}(1 + \cos \Theta_{EL})$$

where $\gamma_{EL}$ is the surface tension of the electrolyte and $\Theta_{EL}$ is the angle of contact between a drop of electrolyte and the binder film.

The binder is chosen on the basis of a combination of two criteria relating to its surface properties.

According to the first criterion, the spreading coefficient $\lambda$ must be negative ($\lambda<0$). In this case the binder forms a discontinuous film enabling electron exchange. If $\lambda$ is positive ($\lambda \geq 0$), the binder forms a continuous film which coats and isolates the active material.

In accordance with the second criterion, the interaction energy $I_{EL}$ must be at least equal to 60 mJ/m² ($I_{EL} \geq 60$ mJ/m²). If $I_{EL}$ is high, the binder wets the electrode more effectively and promotes ion conduction.

The advantage of the present invention is that it allows immediate selection of polymers that can be used as electrode binders without cycling the cells, which is a long and costly method.

The present invention further consists in an electrode for an alkaline electrolyte cell including a current collector and a paste containing an electrochemically active material and a binder having a spreading coefficient $\lambda$ less than zero and an interaction energy $I_{EL}$ of at least 60 mJ/m².

Said binder is preferably chosen from a copolymer of maleic anhydride and styrene and a copolymer of maleic anhydride and a vinyl ether.

Other features and advantages of the present invention will emerge from the following examples which are, of course, given by way of non-limiting illustration, and from the accompanying drawing.

DETAILED DESCRIPTION OF THE PREFERRED EMBODIMENTS

EXAMPLE 1

Figure 1:
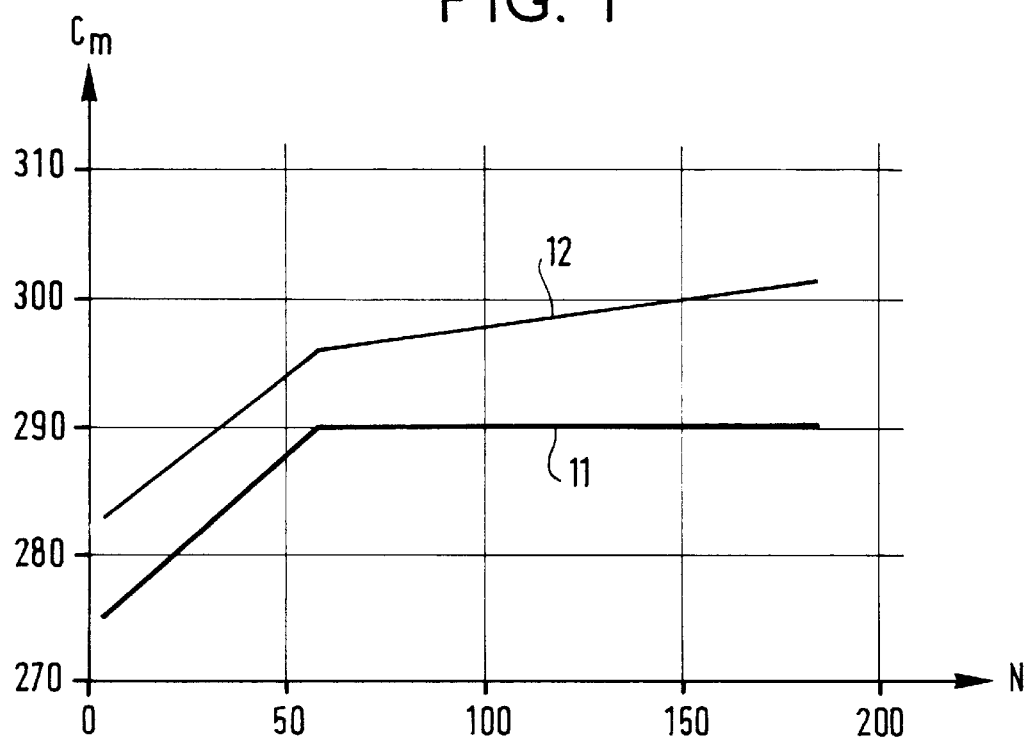
FIG. 1 shows the discharged capacity Q of an electrode in a test cell, expressed in milliampere-hours per gram of hydridable alloy, as a function of the number N of cycles effected.

The method of the present invention was used to characterize a polymer binder which comprised a hydrolyzed copolymer of ethylene and vinyl acetate (EVAH).

The surface energy calculations were based on measured contact angles as previously described. The reference liquids used were diiodomethane as the apolar liquid and water and ethyleneglycol as the polar liquids.

These measurements gave the following results:

$\lambda=+0.1$ mJ/m²

$I_{EL}=80$ mJ/m²

EVAH does not meet the first criterion of the present invention.

An electrode I was prepared including as the electrochemically active material a hydridable alloy of type $AB_n$ in which A was a "MISCHMETAL" and B was nickel partially substituted by Mn, Al and/or Co. The alloy was suspended in an aqueous solution comprising 0.3% by weight of hydroxypropylmethylcellulose (HPMC) and 0.3% by weight of carbon powder. The EVAH polymer binder was added to this suspension in a proportion of 5% by weight of dry matter. The paste obtained, containing 94.4% by weight of active material, was coated onto a nickel sponge conductive support and then dried and rolled to adjust the thickness and the porosity of the electrode.

EXAMPLE 2

The method of the present invention was used to characterize a polymer binder consisting of poly(2-ethylhexyl acrylate (PAEH) in the manner described in example 1.

These measurements gave the following results:

$\lambda=+4$ mJ/m²

$I_{EL}=45$ mJ/m²

PAEH does not meet either criterion of the present invention.

An electrode II was prepared including as the electrochemically active material a hydridable alloy of type $AB_n$ as described in example 1, except that the PAEH polymer binder was added to the suspension in a proportion of 5% by weight of dry matter.

EXAMPLE 3

The method of the present invention was used to characterize a polymer binder consisting of polytetrafluoroethylene (PTFE) in the manner described in example 1.

These measurements gave the following results:

$\lambda=12$ mJ/m²

$I_{EL}=49$ mJ/m²

PTFE does not meet either criterion of the present invention.

An electrode III was prepared including as the electrochemically active material a hydridable alloy of type $AB_n$ in the manner described in example 1, except that the PTFE polymer binder was added to the suspension in a proportion of 5% by weight of dry material.

The PTFE fibrillated very quickly under the conditions of production of the electrode. It formed a discontinuous network, as is usually observed if the spreading coefficient $\lambda$ of the polymer is negative.

EXAMPLE 4

The method of the present invention was used to characterize a polymer binder consisting of a copolymer of styrene and butadiene (SBR) grafted with carboxyl groups, sold by BASF under product reference "LD 417", in the manner described in example 1.

These measurements gave the following results:

$\lambda=-1$ mJ/m²

$I_{EL}=66$ mJ/m²

The carboxylated SBR meets both criteria of the present invention.

An electrode IV was prepared including as the electrochemically active material a hydridable alloy of type $AB_n$ in the manner described in example 1, except that the carboxylated SBR polymer binder was added to the suspension in a proportion of 5% by weight of dry material.

EXAMPLE 5

The method of the present invention was used to characterize a polymer binder comprising a copolymer of styrene and maleic anhydride (SMA) in the manner described in example 1.

These measurements gave the following results:

$\lambda=-15$ mJ/m²

$I_{EL}=93$ mJ/m²

SMA meets both criteria of the present invention.

An electrode V was prepared including as the electrochemically active material a hydridable alloy of type $AB_n$ in the manner described in example 1, except that the SMA polymer binder was added in a proportion of 5% by weight of dry material.

EXAMPLE 6

An electrochemical evaluation of electrodes I through V was carried out. The cycling was conducted in non-sealed storage batteries having a nominal capacity of 3 Ah with electrodes I through V as the negative electrode and nickel hydroxyde electrodes of a type known in itself as the positive electrode. The electrolyte was an 8.7 N alkaline solution, the main constituent of which was potassium hydroxide KOH.

The test was carried out at a temperature of 22° C. under the following conditions:

cycles 1–4 charging at $0.2I_c$ for 7.5 hours, discharging at $0.2I_c$ to 1 volt, cycle 5 charging at $0.2I_c$ for 7.5 hours, discharging at $I_c$ to 0.8 volt, where $I_c$ represents the current needed to charge to 100% the theoretical capacity of the storage battery in one hour. The discharged capacity $D_4$ in cycle 4 and the discharged capacity $D_5$ in cycle 5 were measured, expressed in milliampere-hours per gram of hydridable alloy, and the loss of capacity $\Delta_{4/5}$ for fast charging/discharging was calculated as a percentage between the fourth and fifth cycles.

Table 1 below summarizes the results obtained:

TABLE 1

| binder | EVAH | PAEH | PTFE | SBR | SMA |
|---|---|---|---|---|---|
| $\lambda$ (mJ/m$^2$) | +0.1 | +4 | +12 | −1 | −15 |
| $I_{EL}$ (mJ/m$^2$) | 80 | 45 | 49 | 66 | 93 |
| | ↓ | ↓ | ↓ | ↓ | ↓ |
| electrode | I | II | III | IV | V |
| $D_4$ (mAh/g) | 265 | 273 | 294 | 289 | 303 |
| $D_5$ (mAh/g) | 221 | 191 | 259 | 251 | 283 |
| $\Delta_{4/5}$ (%) | 20 | 30 | 12 | 13 | 7 |

Note that the initial capacities $D_4$ are higher and that the capacity losses $\Delta_{4/5}$ for fast charging/discharging are lower for binders IV and V, which have a negative spreading coefficient $\lambda$, compared to binders I and II, the spreading coefficient $\lambda$ of which is positive. The PTFE behaves like a binder with a negative spreading coefficient $\lambda$.

EXAMPLE 7

An electrode VII was prepared including as the electrochemically active material a hydridable alloy of type $AB_n$ where A was a "MISCHMETAL" and B was nickel partially substituted by Mn, Al and/or Co.

The alloy was suspended in an aqueous solution containing 0.3% by weight of carbon powder 0.3% by weight of hydroxypropylmethylcellulose (HPMC). The PTFE polymer binder was added to the suspension in a proportion of 1.5% by weight of dry matter.

The paste obtained, containing 98.1% by weight of active material, was coated onto a nickel sponge conductive support and then dried and rolled to adjust the thickness and the porosity of the electrode.

EXAMPLE 8

An electrode VIII was prepared including as the electrochemically active material a hydridable alloy of type $AB_n$ where A was a "MISCHMETAL" and B was nickel partially substituted by Mn, Al and/or Co.

The alloy was taken up into suspension in an aqueous solution containing 0.3% by weight of carbon powder and 0.3% by weight of hydroxypropylmethylcellulose (HPMC). The SBR polymer binder grafted by carboxyl groups, sold by BASF under the product reference "LD 417" was added to the suspension in a proportion of 0.3% by weight of dry material.

The paste obtained, containing 99.1% by weight of active material, was coated onto a nickel foam conductive support and then dried and rolled to adjust the thickness and the porosity of the electrode.

EXAMPLE 9

An electrochemical evaluation of electrodes VII and VIII was carried out. The cycling was performed in a test cell in which the negative electrode VII or VIII was positioned facing a nickel counter-electrode of a type known in itself, from which it was separated by a nonwoven polypropylene separator. The cell contained an electrolyte consisting of an 8.7 N alkaline solution in which the principal constituent was potassium hydroxyde KOH.

The test was conducted at a temperature of 22° C. under the following conditions:

charging at $I_c$ for 1.05 hour, then discharging at $I_c$ for 0.8 hour.

The discharged capacity Q expressed in milliamperes-hours per gram of hydridable alloy was measured. FIG. 1 shows the capacity Q as a function of the number of cycles. After 150 cycles, the performance of the electrode VII (curve 11) containing PTFE, the interaction energy $I_{EL}$ of which was below 60 mJ/m$^2$, was inferior to that of electrode VIII (curve 12), containing carboxylated SBR, the interaction energy $I_{EL}$ of which was greater than 60 mJ/m$^2$.

Sealed storage batteries having a nominal capacity of 120 Ah, negative electrodes in the form of electrodes VII and VIII and positive electrodes consisting of nickel hydroxyde electrodes of a type known in itself were then cycled. The electrolyte was an 8.7 N alkaline solution, the main constituent of which was potassium hydroxyde KOH.

The test was conducted at a temperature of 22° C. under the following conditions:

charging at $0.33I_c$ for 3 hours, then at $0.1I_c$ for 2 hours, discharging at $I_c$ for 0.7 hours.

Figure 2:
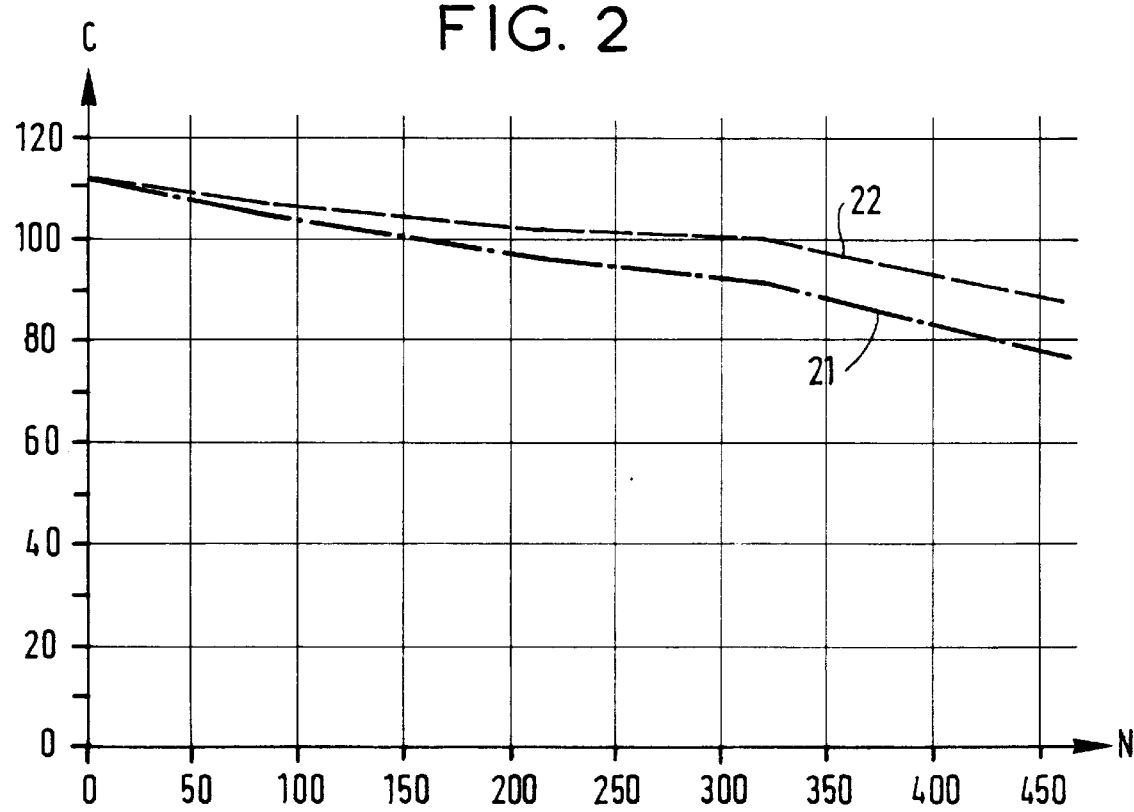
FIG. 2 shows the discharged capacity C of a sealed storage battery, expressed in milliampere-hours, as a function of the number N of cycles effected.

The capacity C discharged by the accumulator expressed in milliampere-hours was measured. FIG. 2 shows the capacity C as a function of the number of cycles for the storage battery containing the electrode VII (curve 21) and the storage battery containing the electrode VIII (curve 22). Note that the capacity of the electrode VII containing PTFE decreased faster than that of the electrode VIII containing carboxylated SBR. This confirms the results observed previously.

Finally, the gases contained in the two sealed storage batteries, respectively including the electrodes VII and VIII, like those described previously but having nominal capacity of 10.8 Ah, were analyzed. These storage batteries were cycled at a temperature of 22° C. under the following conditions:

charging at $0.1I_c$ for 7.5 hours, discharging at $0.2I_c$ to 1 volt.

When the pressure had stabilized, the gases were sampled and analyzed, and the following results were obtained:

TABLE 2

| electrode | VII | VIII |
|---|---|---|
| stabilized pressure (bars) | 0.78 | 0.46 |
| $O_2$ | 50% | 70% |
| $H_2$ | 50% | 30% |

Far less hydrogen was evolved for electrode VIII, containing the SBR grafted with carboxylic groups, than for electrode VII, containing PTFE, indicating that electrode VIII was wetted more effectively by the electrolyte.

There is claimed:

1. A method of characterizing a polymer binder for cell electrodes in contact with an electrolyte including a current collector and a paste containing an electrochemically active material and said binder, comprising the following steps:

(a) calculating a spreading coefficient $\lambda$ of said binder on said active material from a measured angle of contact between standard liquids and said active material and said binder, respectively, (b) calculating an interaction energy $I_{EL}$ of said binder with said electrolyte from a measured angle of contact between said electrolyte and said binder, and (c) selecting said binder such that said spreading coefficient $\lambda$ is less than zero and said interaction energy $I_{EL}$ is at least 60 $mJ/m^2$.

2. An electrode for an alkaline electrolyte cell including a current collector and a paste containing an electrochemically active material and a binder having a spreading coefficient $\lambda$ less than zero and an interaction energy $I_{EL}$ of at least 60 $mJ/m^2$.

3. The electrode claimed in claim 2 wherein the binder is (i) a copolymer of maleic anhydride and styrene, or (ii) a copolymer of maleic anhydride and a vinyl ether.

* * * * *